United States Patent [19]

Heinzman et al.

[11] Patent Number: 5,534,642

[45] Date of Patent: Jul. 9, 1996

[54] SYNTHESIS OF AMIDO ACIDS FROM CARBOXYLIC ACIDS AND LACTAMS

[75] Inventors: Stephen W. Heinzman, Wyoming; Jeffrey S. Dupont, Fairfield; William C. Tettenhorst, Okeana, all of Ohio

[73] Assignee: The Procter & Gamble Company, Cincinnati, Ohio

[21] Appl. No.: 392,599

[22] Filed: Feb. 23, 1995

Related U.S. Application Data

[62] Division of Ser. No. 121,013, Sep. 14, 1993, Pat. No. 5,414,099.

[51] Int. Cl.⁶ ........................................................ C11D 1/28
[52] U.S. Cl. .............................. 554/98; 554/45; 554/48; 554/68; 554/69; 252/188.280
[58] Field of Search .................................. 554/98, 68, 69, 554/48, 45

[56] References Cited

U.S. PATENT DOCUMENTS 4,681,592  7/1987  Hardy et al. ............................... 8/111

FOREIGN PATENT DOCUMENTS 506308   9/1992  European Pat. Off. ...... C07C 309/42
1177099  1/1970  United Kingdom ............ C07C 99/06

*Primary Examiner*—C. Warren Ivy
*Assistant Examiner*—Deborah D. Carr
*Attorney, Agent, or Firm*—K. W. Zerby; J. J. Yetter; J. C. Rasser

[57] ABSTRACT

Chemical synthesis of amido acids, and their conversion to amido acid phenyl ester sulfates for use as bleach activators, starting from carboxylic acids and lactams.

17 Claims, No Drawings

SYNTHESIS OF AMIDO ACIDS FROM CARBOXYLIC ACIDS AND LACTAMS

FIELD OF THE INVENTION

This is a division of application Ser. No. 08/121,013, filed on Sep. 14, 1993, now U.S. Pat. No. 5,414,099.

The present invention relates to the chemical synthesis of amido acids, and their conversion to amido acid phenyl ester sulfonates for use as bleach activators. This conversion can be direct by reaction of the amido acids with phenol sulfonic acid derivatives; or by the conversion of the amido acids to their phenyl ester form and then the conversion of said amido phenyl esters into their sulfonated form; or by the conversion of the amido acids to their anhydride and then reaction with sodium phenolsulfonate to form the amido acid phenyl ester sulfonates.

BACKGROUND OF THE INVENTION

The synthesis of ingredients for use in low unit cost consumer goods such as laundry detergents, fabric softeners, hard surface cleansers, and the like, is of considerable interest to manufacturers. Indeed, while formularies and patents are filled with listings of prospective ingredients for use in such products, the reality is that many such ingredients are simply too expensive for day-to-day use. This expense is often due either to the cost of the raw materials used to make such ingredients, or to the complex reaction and processing chemistry which is required in their manufacture. Accordingly, manufacturers have conducted a continuing search for both inexpensive raw materials and simple reaction sequences which can produce high performance, high value ingredients at the lowest possible cost.

The amido acids comprise one class of chemicals whose amido and carboxylate functional groups suggest their use as surfactants (i.e., sarcosinates), fabric softeners, antistatic agents and the like. Moreover, the amido acids constitute a basic raw material for the amido phenyl ester sulfonate class of chemicals which can serve as bleach activators in laundry detergents and other types of bleach-containing cleaning compositions. Such activators have several desirable attributes such as excellent bleaching performance with minimal color damage on fabric dyes, good washing machine compatibility and a good odor profile in the wash. On the positive side, the amido acids and their aforementioned derivatives are potentially obtainable from inexpensive raw materials. Unfortunately, the synthesis of certain amido acids is somewhat complicated and can involve the use of solvents, with additional problems associated with recycle streams and the like. Problems can also arise with the formation of undesirable colored by-products. Moreover, the conversion of the amido acids to their phenyl ester form is not straightforward and can be surprisingly problematic.

The present invention provides a simple, one-step method for the synthesis of amido acids. It also provides four methods for converting amido acids into amido acid phenyl ester sulfonates which are suitable for use as bleach activators in laundry detergents, and the like. The first method is a simple, one-step esterification of amido acid with phenol to provide an amido acid phenyl ester which can subsequently be reacted with $SO_3$ and neutralized in conventional fashion to give amido acid phenyl ester sulfonates. The second prepares the amido acid phenyl ester by transesterification of ester derivatives of phenol followed by the conversion to the amido acid phenyl ester sulfonates as described for the first method. The third method involves transesterification of ester derivatives of phenol sulfonic acid or salt, preferably acetoxybenzenesulfonic acid or salt (typically sodium or potassium), with amido acid to provide amido acid phenyl ester sulfonates directly. The fourth method involves making the anhydride of the amido acid and reacting this anhydride with sodium phenolsulfonate to also produce amido acid phenyl ester sulfonate directly.

The individual reaction sequences herein proceed in acceptable yields (typically 60%, and higher) and, importantly, result in products with minimal discoloration. The reactions may be conducted without added solvents, i.e., the reactants act as solvents. Hence, for many purposes the reaction products need not be extensively purified which further improve the overall economics of the processes.

BACKGROUND ART

The boric acid-catalyzed esterification of certain phenols is described by W. Lowrance, Jr., in *Tetrahedron Letters* No. 37 pp. 3453–3454 (1971). See U.S. Pat. No. 2,956,068, Dohr et al, Oct. 11, 1960, for one type of reaction of lactams with carboxylic acids. A process for preparing certain benzenesulfonate salts appears in U.S. Pat. No. 5,153,541, Amini and Dumas, Oct. 6, 1992.

SUMMARY OF THE INVENTION

The present invention encompasses a method for preparing amido acids of the formulas

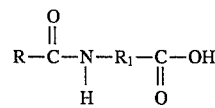

and

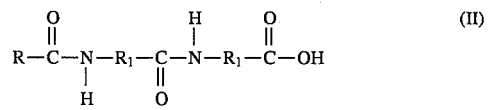

wherein R is a $C_1$ or higher hydrocarbyl substituent and $R^1$ is $C_2$–$C_{10}$ hydrocarbylene substituent, and $R^1$ is preferably —$(CH_2)_x$— wherein x is from 2 to 10, by reacting a carboxylic acid of the formula

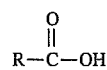

with a lactam of the structure

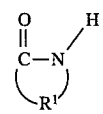

wherein $R^1$ is as described before, in the presence of an acid catalyst, preferably a member selected from the group consisting of bode acid, sulfuric acid, methanesulfonic acid, trifluoromethanesulfonic acid, phosphoric acid and aryl sulfonic acids such as toluenesulfonic acid and phenolsulfonic acid, and mixtures thereof. A preferred acid catalyst is boric acid, methanesulfonic acid or toluenesulfonic acid. If sulfuric acid is used, it is preferred that it be about a 50%–70% concentrated aqueous sulfuric acid, most preferably 70% aqueous $H_2SO_4$.

The preferred method for preparing said amido acids is conducted at a temperature from about 150° C. to about 250° C., especially from about 200° C. to about 235° C.

In one preferred embodiment, the method herein employs a lactam selected from caprolactam and valerolactam. In a preferred aspect, the carboxylic acid has substituent R as $C_6$–$C_{17}$.

In order to minimize polymerization of the lactam, it is preferred to conduct the reaction herein at a molar ratio of the fatty acid reactant to the lactam reactant of at least about 1.5:1. In a highly preferred mode, the molar ratio of the fatty acid:lactam is in the range of about 2:1 to about 10:1 and the reaction is conducted without added solvent.

The invention also encompasses a method for preparing amido acid phenyl esters of the formulas

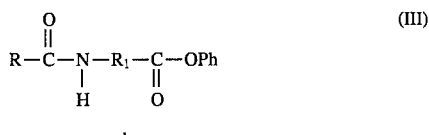

and

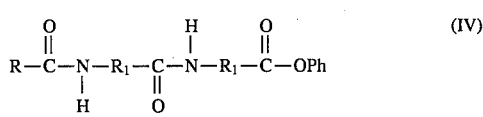

wherein R and $R^1$ are as described herein before, comprising reacting an amido acid having Formulas (I) and/or (II) above with phenol in the presence of a strong catalyst and boric acid to produce the amido acid phenyl esters of Formulas (III) and (IV), respectively.

In this method the strong acid (non-boric acid) catalyst is a member selected from the group consisting of sulfuric acid, methanesulfonic acid, trifluoromethanesulfonic acid, toluenesulfonic acid, phosphonic acid and mixtures thereof. Preferably, the mole ratio of boric acid to the strong acid catalyst is at least about 1:1, more preferably at least about 1:3.6. Preferably, the mole ratio of amido acid to strong acid catalyst is at least about 1:0.05 and more preferably about 1:0.25. This esterification reaction is preferably conducted at a temperature in the range from about 180° C. to about 210° C., and is most preferably conducted without added solvent.

The esterification herein is preferably conducted at a temperature of about 180°–190° C. in the absence of solvent, with 98% sulfuric acid as the acidic catalyst, and at a mole ratio of boric acid to sulfuric acid of at least about 1:3.6. Preferably, an excess of phenol is used, typically a phenol:amido acid mole ratio of about 5:1 to about 20:1.

The invention also encompasses a method for preparing amido acid phenyl esters of the formula (II) comprising reacting an amido acid having Formula (I) above with a phenyl ester of a lower molecular weight carboxylic acid moiety, preferably phenyl acetate, in the presence of a basic catalyst. The basic catalyst can be selected from the group consisting of carboxylate salts, carbonates, imidazole and mixtures thereof. Preferably, the mole ratio of basic catalyst to amido acid is at least about 0.001:1, more preferably at least about 0.01:1. Preferably, the mole ratio of amido acid to phenyl ester is at least about 1:1 and more preferably about 3:1. This transesterification reaction is preferably conducted at a temperature in the range from about 160° C. to about 210° C., and is most preferably conducted without added solvent.

As an overall proposition, the invention herein also provides a method for preparing bleach activators comprising sulfonating and neutralizing an amido acid phenyl ester of Formulas (III) and/or (IV) prepared according to the foregoing processes to produce, respectively, amido acid phenyl ester sulfonates of the formulas:

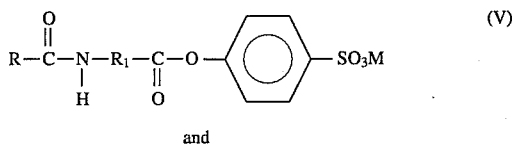

and

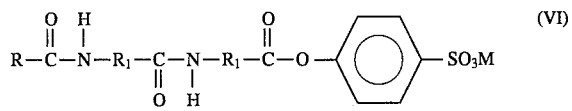

wherein R and $R^1$ are as described hereinbefore, the amido acid phenyl ester sulfonate is predominantly para-substituted (as pictured) although ortho-substitution is acceptable, and M is a cationic moiety, preferably a mono- or divalent metal salt (e.g., potassium, sodium) or hydrogen, which for use of these compounds as bleach activators should be substantially free of transition metal ions (known to cause instability of peroxy compounds).

The invention also encompasses a method for preparing amido acid phenyl ester sulfonates of the Formulas (V) and (VI) above by reacting an amido acid of Formulas (I) and/or (II) above with an ester derivative of phenol sulfonic acid or salt of the formula:

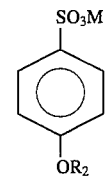

wherein M is a cationic moiety as described herein before and $R^2$ is an acid moiety, preferably a lower ($C_2$–$C_5$) molecular weight carboxylic acid moiety such as the most preferred acetic acid moiety. When M is hydrogen, the addition of catalyst is not required; when M is a metal salt, this transesterification reaction can utilize an acid or base catalyst.

Reaction temperatures for this transesterification reaction are at least about 150° C., preferably from about 180° C. to about 220° C., for reactions with acetoxy benzene sulfonic acid sodium salt. Lower reaction temperatures, from about 140° C. to about 180° C., are preferred for reactions with acetoxy benzene sulfonic acid.

The invention also provides a method for preparing amido acid phenyl ester sulfonates of the Formulas (V) and (VI) above by reacting an amido acid of Formulas (I) and/or (II) above with a lower ($C_4$–$C_{10}$) molecular weight carboxylic acid anhydride (e.g., $(R^3CO)_2O$, wherein each $R^3$ is the same or different $C_1$–$C_4$ hydrocarbyl substituents), preferably acetic anhydride, to form the amido acid anhydride. The amido acid anhydride is then reacted with phenolsulfonate salt (preferably the sodium salt) to form the desired amido acid phenyl ester sulfonates.

The amido acid anhydride is prepared by reacting amido acid with the lower molecular weight carboxylic acid anhydride in a molar ratio ranging from about 1:3 to about 5:1. Reaction temperatures are from about 70°–110° C. with reaction times of about 1–18 hr. Catalysts such as sodium acetate, sodium carbonate, sodium bicarbonate, imidazole, or methanesulfonic acid can be used. At the end of the reaction, carboxylic acid and/or excess carboxylic acid anhydride, such as acetic acid and/or excess acetic anhydride, are removed by distillation.

The crude amido acid anhydride mixture is then reacted with anhydrous phenolsulfonate salt in a molar ratio of about 1:1. Reaction temperatures are from about 100°–200° C. with reaction times of about 1–6 hr. Basic catalysts such as sodium acetate or imidazole can be used. If the crude amido acid anhydride contains excess amido acid, then solvent is not needed. If excess amido acid is not present in the amido acid anhydride, solvents such as dimethylformamide, toluene, or xylenes can be used.

All percentages, ratios and proportions herein are on a mole basis, unless otherwise specified. All documents cited are incorporated herein by reference.

DETAILED DESCRIPTION OF THE INVENTION

Shown herein after are the reaction Sequence (1) illustrating the synthesis of the amido acids, and reaction Sequence (2a) and (2b) illustrating their conversion to the phenyl ester form. Sequence (3) illustrates the conventional sulfonation step, which typically includes base neutralization to prepare the salt form of the amido phenyl ester sulfonate class of bleach activators. Sequences (4a), (4b), and (5) illustrate alternative methods for preparing the amido phenyl ester sulfonate directly from the amido acid prepared by Sequence (1). The reaction sequences as illustrated employ octanoic acid and caprolactam, but this is only by way of illustration and not limitation, as will be seen hereinafter.

Sequence 1

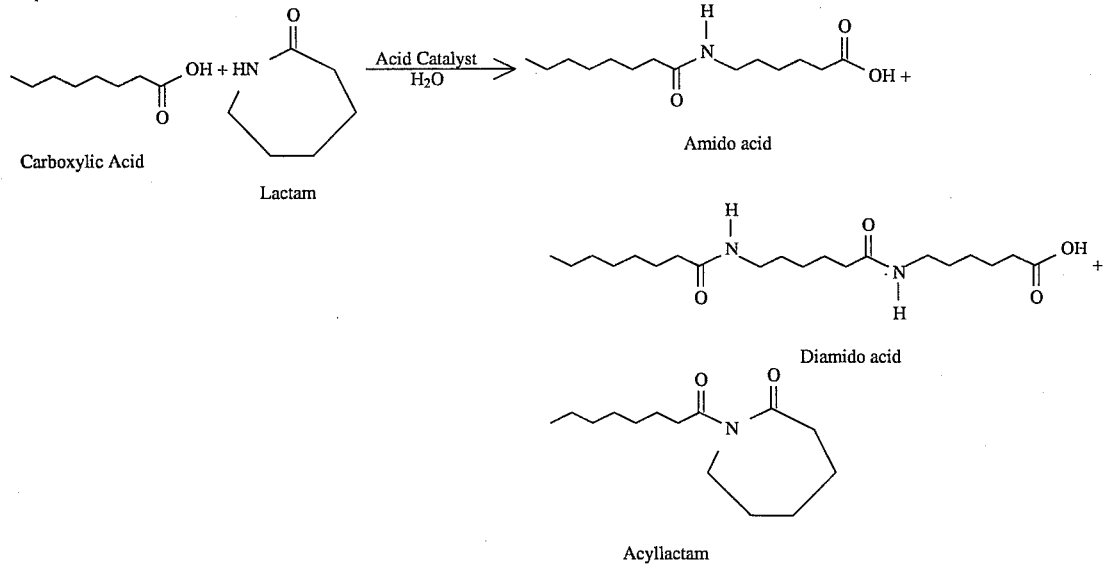

Sequence 2a

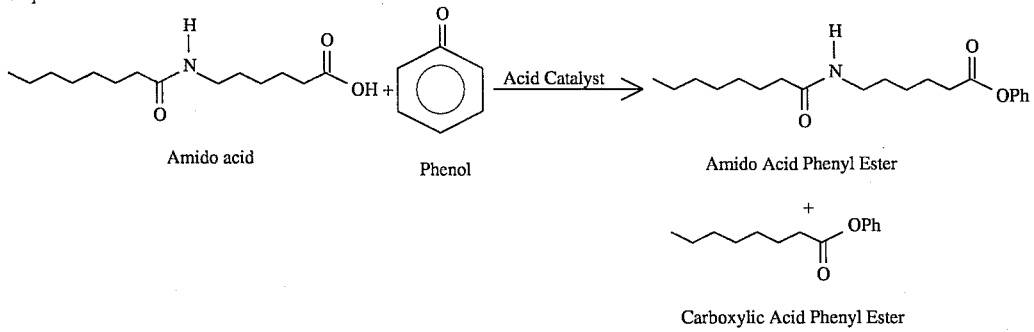

Sequence 2b

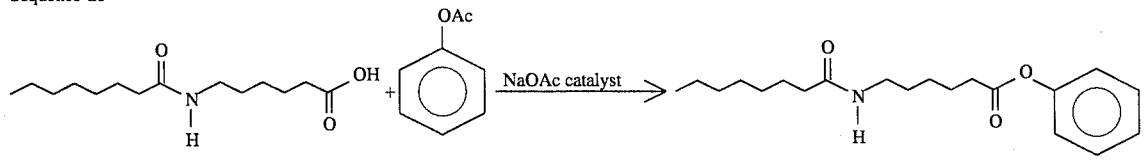

Sequence 3

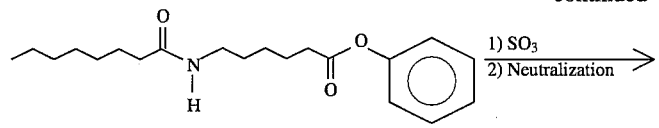
Amido Acid Phenyl Ester
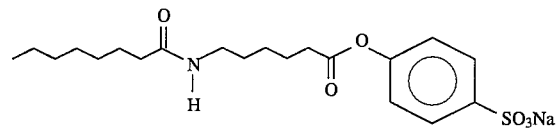
Amido Acid Phenylestersulfonate
Sequence 4a
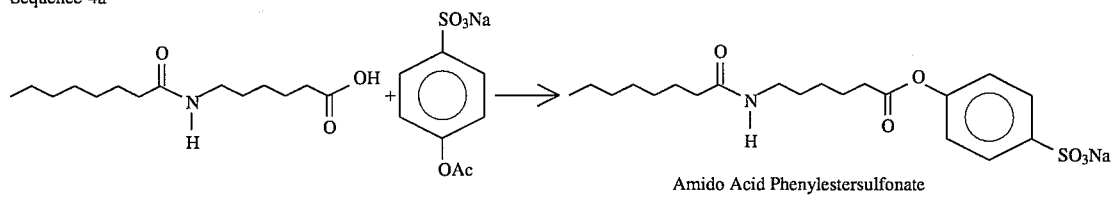
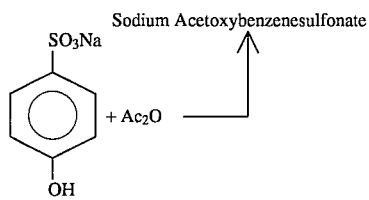
Sequence 4b
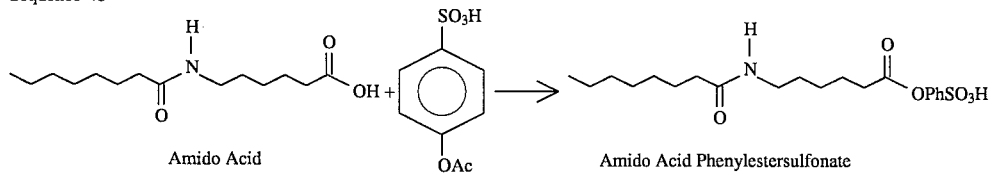
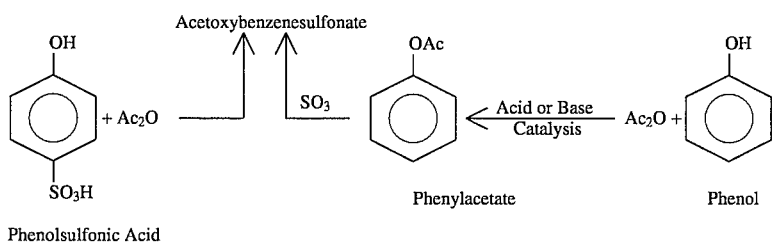
Sequence 5
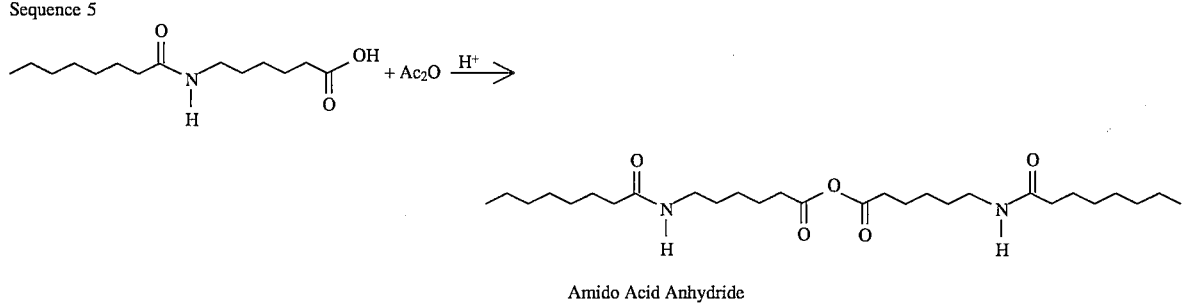
Amido Acid Anhydride

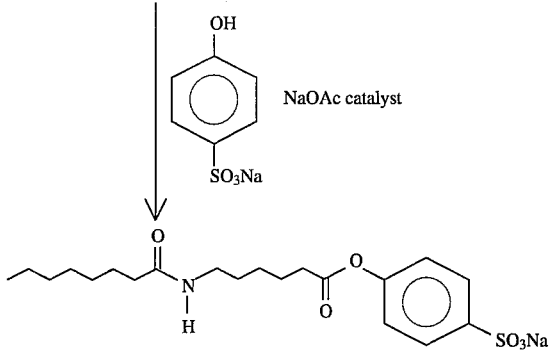

The following is by way of illustration, and not limitation, of conditions, equipment and the like, useful in Sequences 1, 2, 3, 4, and 5 of the instant process.

Sequence 1. The carboxylic acid reactant can be selected from straight chain aliphatic, branched chain aliphatic, saturated or unsaturated, aromatic, heteroaromatic, ethercarboxylic and cycloaliphatic carboxylic acids. Nonlimiting examples include the following carboxylic acids: acetic, propionic, butyric, caprylic, caproic, nonanoic, 3,5,5-trimethylhexanoic, decanoic, lauric, myristic, palmitic, stearic, oleic, linoleic, behenic, 2-methyl-undecanoic, 2-butyl-octanoic, 2-ethyl-hexanoic, alkyl- and alkenylsuccinic, adipic, cyclohexyl, $C_8(EO)_2CO_2H$, benzoic, chloro-benzoic, nitrobenzoic, naphthenic, abietic, nicotinic, 2-pyridine-carboxylic, terephthalic, phthalic, and mixtures thereof.

The lactam reactant in Sequence 1 can be, for example: butanolactam, valerolactam, caprolactam, heptanolactam, decanolactam, dodecanolactam, and mixtures thereof.

The acid catalyst in Sequence 1 can be, for example: boric, sulfuric, phosphoric, perchloric, alkylsulfonic acids such as methanesulfonic and trifluoromethanesulfonic, arylsulfonic acids such as benzenesulfonic, toluenesulfonic, naphthalenesulfonic, phenolsulfonic, and strong acid ion-exchange resins such as AMBERLYST and NAFION. If a strong acid is used which has oxidizing properties (e.g., sulfuric) it is preferred to add water in order to maintain acceptable color of the final product. As noted, 70% $H_2SO_4$ is preferred over concentrated $H_2SO_4$ for this reason. However, nonoxidizing acids such as toluenesulfonic, methanesulfonic, and phosphoric acid do not cause as much color formation and water is not needed.

The acid catalyst in Sequence 1 is employed typically in the range of at least about 0.001 mole, preferably from about 0.01 mole to about 0.1 mole, based on the moles of lactam reactant being used. (The carboxylic acid reactant is present in excess, and is thus not used to calculate the amount of catalyst.)

Water (from about 0.1 to about 1, preferably from about 0.2 to about 0.4, molar equivalents based on the lactam) may be added in Sequence 1 to increase the conversion of caprolactam to amido acid. The addition can occur at the beginning of the reaction or preferably after 2–4 hours when a maximum amount of amido acid and acyl caprolactam has been formed. The increase in conversion is believed to result from hydrolysis of acyl caprolactam byproduct to amido acid. The conversion is optimum at room temperature in the presence of a strong acid such as methanesulfonic acid. It is believed that selective hydrolysis of the ring amide bond in acyl caprolactam occurs. Although room temperature is preferred for highest conversion, reaction times are long (1–2 days). Higher temperatures can be used for quicker reaction times, but the conversion is not as high.

The reaction conditions in Sequence 1 include the following. Any air in the system causes a drastic darkening of the reaction mixture. Consequently, an inert gas (nitrogen is convenient) is sparged through the reaction mixture during Sequence 1. Inert gases such as argon, or the like, can also be used. The objective is to provide a nonoxidizing reaction system in order to minimize the formation of colored contaminants.

The highly acidic nature of the catalyst used in Sequence 1 requires inert reaction vessels, such as those made from, or lined with, glass, quartz, high quality stainless steel, and the like. It is highly preferred that all mixers, inlet ports, and the like, also be constructed from inert materials.

Reaction times can vary, of course, depending on the reactant volumes being employed. However, as a general rule for reactions in the 100 mls size range, a reaction time in the range from about 2 hours to about 4 hours is sufficient.

Reaction temperatures in Sequence 1 will typically be above about 150° C. and below about 250° C., and are preferably in the range from about 185° C. to about 240° C. For low boiling carboxylic acids such acetic acids, it may be appropriate to use a pressure vessel in order to achieve the desired reaction temperature.

Reaction stoichiometry in Sequence 1 employs an excess of carboxylic acid, which is necessary to prevent oligomerization of the lactam, especially caprolactam. To illustrate this point further, for 1 mole of caprolactam reactant, from about a 1.5 to a 10 mole excess of the carboxylic acid is used. Similar considerations hold with the other lactam reactants and typically at least a 0.1 mole excess of the carboxylic acid is employed. Excess carboxylic acid and any unreacted lactam can be removed from the reaction mixture by vacuum distillation and recycled. (It may be desirable to neutralize the acid catalyst before distillation to prevent oligomers from forming.)

Sequence 2a. The preparation of the phenyl esters of carboxylic acids, especially the amido acids, is as follows. Useful carboxylic acid reactants in Sequence 2 include all of the amido acids prepared per Sequence 1. The phenol reactant includes phenol, itself, as well as alkyl substituted phenols such as cresols and phenol derivatives such as phenolsulfonates.

The strong acid catalyst used in Sequence 2 can be any of the strong protonic acid catalysts used in Sequence 1. Sulfuric acid (98%) is convenient, inexpensive and preferred. Under the process conditions the sulfuric acid sulfates the phenol in situ, so that the strong acid catalyst is at least partially the phenolsulfonic acid.

While not intended to be limiting by theory, it is believed that the mechanism of ester formation involves the formation of a triphenol borate ester by a reaction of a borate material with the phenolic material; followed by exchange of phenol for carboxylic acid to form a carboxylic/boric anhydride species; followed by some manner of phenol displacement of the borate ester from the carboxylic-boric anhydride species; followed by exchange of water to form the borate species and reform the triphenol borate active catalyst agent. Accordingly, any borate or boric acid material, or precursor thereof, which results in the formation of a triphenol borate ester with phenol or substituted phenols can be used herein. Typical examples of such materials include boric acid, boric acid precursors, boric acid esters, for example, materials such as borax, tributylborate, triphenylborate, and the like. A wide variety of borate materials are available from standard, commercial sources. Boric acid is a convenient and inexpensive catalyst for use in Sequence 2.

It is further hypothesized that the presence of the strong protic acids probably plays at least three different roles in the esterification mechanism: catalysis of the initial borate ester formation; catalysis of phenol displacement of the borate species; and as a desiccant for water which is produced in the reaction.

With regard to reaction conditions, in Sequence 2 any air in the system causes a drastic darkening of the reaction mixture, just as in Sequence 1. Consequently, nitrogen sparging or sparging with another inert gas in order to provide a nonoxidizing condition is preferably used. Again, as in Sequence 1, it is preferred in Sequence 2 to use an inert reaction vessel such as those made from glass, quartz, stainless steel, or the like.

Reaction temperatures of at least 150° C., preferably from about 180° C. to about 200° C., are preferred, and reaction times are similar to those disclosed for Sequence 1, typically 2 to 4 hours. Water (which may be present in the starting materials) is removed during the first 30 minutes of the reaction by azeotropic distillation of phenol/water. The presence of water is detrimental to the overall yield because it can result in the hydrolysis of the amide linkage of the amido acids and/or amido acid phenol esters.

It has been determined that excess phenol or substituted phenol is necessary to drive the reaction to completion. Less excess phenol is viable if azeotropic distillation is carried out for the entire reaction time. Typically, about a 5 mole excess of said phenol or substituted phenol is employed, preferably from about 8 to about 12 mole excess. Based on the amido acid portion of one mole, the strong acid catalyst proportion is at least about 0.01 mole, preferably from about 0.25 mole to about 0.5 mole. The boric acid is used at levels from about 0.01 mole to about 0.07 moles, based on the amido acid reactant.

Following the esterification reaction, excess phenol is removed from the reaction mixture by vacuum distillation or other suitable means, and can be recycled. The remaining reaction product consists of the desired amido acid phenol ester, carboxylic acid phenyl ester and unreacted amido acid. This reaction product can be purified prior to sulfonation, or can be sulfonated without further purification since the contaminants are compatable with many detergent compositions.

Sequence 2b Transesterification of a phenyl ester of a lower ($C_2$-$C_5$) molecular weight carboxylic acid moiety, preferably phenyl acetate, with amido acid in the presence of a basic catalyst provides amido acid phenyl ester in good yield. The basic catalyst can be selected from the group consisting of carboxylate salts, carbonates, imidazole and mixtures thereof. Preferably, the mole ratio of basic catalyst to amido acid is at least about 0.001:1, more preferably at least about 0.01:1. Preferably, the mole ratio of amido acid to phenyl ester is at least about 1:1 and more preferably about 3:1. This transesterification reaction is preferably conducted at a temperature in the range from about 160° C. to about 210° C., and is most preferably conducted without added solvent.

Sequence 3. Sulfonation of the amido acid phenol ester can be conducted using sulfur trioxide, sulfur trioxide vapor, chlorosulfonic acid, sulfur trioxide complexes, oleum, sulfamic acid, and the like, plus other typical sulfonating agents. Reaction can be carried out without solvent, or, if desired, can be conducted in solvents such as sulfur dioxide, methylene chloride, ethylene dichloride, carbon tetrachloride, fluorotrichloromethane, and the like. It is preferred to run the sulfonation reaction of Sequence 3 without solvent. Of course, unsaturated materials should be avoided in the reaction mixture, primarily due to color formation.

As in the case of Sequences 1 and 2, the sulfonation reaction of Sequence 3 is highly acidic and inert reaction vessels are again used. Reactors can be of the continuous film or continuous cascade types, for example, when sulfur trioxide is used as the sulfonating reactant, it is preferably introduced in an inert gas stream (nitrogen or dry air) coming 1–20% by weight sulfur trioxide. Reaction temperatures are typically 20° C. to 200° C. with reaction times of from 5 to 180 minutes (based on 1 mole of amido acid phenyl ester being sulfonated). For a typical run, the amido acid phenyl ester is present at a 1 mole level and this sulfonating agent used at a 0.9–1.5 mole level. Product work-up involves neutralizing the crude reaction mixture to pH 4–6 with base such as sodium bicarbonate, sodium acetate, sodium formate, or the like.

Sequence 4. Amido acid phenyl ester sulfonate can also be made by transesterification of acetoxybenzenesulfonic acid or its salt (typically sodium or potassium) with amido acid. If acetoxybenzenesulfonic acid sodium salt is used, then a 3–4 mol equivalent excess of amido acid is necessary to act as solvent. If acetoxybenzenesulfonic acid is used, then a 1.2 mol equivalent excess of amido acid is sufficient. Either base or acid catalysis promotes the transesterification of acetoxybenzenesulfonic acid sodium salt; sodium acetate or sulfuric acid are typically used. Transesterification with acetoxybenzenesulfonic acid does not require a catalyst.

A stream of inert gas is passed over the reaction so as remove acetic acid as it is formed and provide a nonoxidizing environment. As in Sequence 3, inert reaction vessels are preferred.

Reaction temperatures of at least about 150° C., preferably from about 180° C. to about 220° C., are necessary for transesterification with acetoxybenzenesulfonic acid sodium salt. Lower reaction temperatures (from about 140° C. to about 180° C.) are preferred when using acetoxybenzenesulfonic acid because less side products are formed. Reaction times are 1–4 hours for either transesterification.

Acetoxybenzenesulfonic acid sodium salt can be prepared from reaction of excess acetic anhydride with dry phenolsulfonic acid sodium salt. Acetic anhydride or acetic acid can serve as a solvent. Acetoxybenzenesulfonic acid can be made from reaction of acetic anhydride with dry phenolsulfonic acid. Alternatively, it can be made from sulfonation of phenyl acetate with sulfur trioxide or chlorosulfonic acid.

Following transesterification with acetoxybenzenesulfonic acid sodium salt, the excess amido acid must be removed from product and recycled. This can be achieved by grinding the reaction product into small particles and dissolving the amido acid with a solvent. The solid amido acid phenyl ester sulfonate is then collected by filtration. Several solvents are suitable: cold methanol, butanol at 60° C., toluene and xylenes at 100° C., octanoic acid. Product workup after transesterification with acetoxybenzenesulfonic acid involves neutralizing the crude reaction mixture as in Sequence 3.

Sequence 5. Formation of the amido acid anhydride is accomplished by reacting amido acid with acetic anhydride. Reaction temperatures between about 70° and about 110° C. are favored to avoid acylation of the amide nitrogen. The molar ratio of amido acid to acetic anhydride is from about 1:3 to about 5:1. If the molar ratio is about 3.0:1 or higher, it is not necessary to add a solvent for the reaction with sodium phenolsulfonate. After a reaction time of about 1–18 hr, acetic acid and/or acetic anhydride are distilled from the reaction mixture to give the crude amido acid anhydride. Sodium phenolsulfonate is then added in about a 1:1 molar ratio to the amido acid anhydride and the reaction is heated at from about 100°–200° C. for about 1–18 hr. Toluene or xylenes can be used as solvents for this reaction. At the end of the reaction, unreacted amido acid can be removed from the amido acid phenyl ester sulfonate by washing with a hot solvent (eg, toluene) which melts or dissolves the amido acid, but does not dissolve the amido acid phenyl ester sulfonate.

It is to be understood that the overall process herein provide several advantages over other processes. For example, with respect to the amido acids, the usual synthesis of amido acids employs the reaction of fatty acid chlorides with an amino acid in an aqueous alkaline medium. There are substantial cost advantages over the present development, inasmuch as fatty acids and caprolactams are less expensive starting materials than fatty acid chlorides and aminocaproic acid. In the usual synthesis, sodium chloride waste is generated, which is not a factor in the present invention. Moreover, the process herein has fewer synthetic steps and does not involve large amounts of water, which would have to be removed prior to Sequence 2. Sequence 1 of the present process produces nearly exclusively amido and diamido acids and not lactam-derived higher oligomers. The present invention also has shorter reaction times, lower temperatures and does not require pressures as the reactions of U.S. Pat. No. 2,956,068.

With regard to the amido acid phenyl ester synthesis of Sequence 2, esterification of the amido acid can be achieved by forming the acid chloride of the amido acid and subsequently reacting it with phenol or phenolsulfonate. This reaction has the same problems as those mentioned above for the amido acid synthesis. While esterification of conventional carboxylic acids with phenols using boric/sulfuric acid has been described in the Lowrance article, cited hereinabove, the reaction conditions described by Lowrance fail to esterify amido acids in any reasonable yields. For example, the present process employs much higher reaction temperatures than those disclosed by Lowrance, said temperatures being achieved by using phenol as the azeotroping agent. Moreover, much higher amounts of sulfuric acid catalyst are used herein, which promotes the desired reaction while reducing side reactions.

In earlier described methods of forming phenyl ester sulfonates (e.g., European Patent Application No. 105,673, published Apr. 18, 1984), a fatty acid anhydride is formed (from reaction with acetic anhydride) and then reacted with phenolsulfonic acid sodium salt. It should be noted that reaction of amido acid with acetic anhydride under the described conditions results not only in formation of amido acid anhydride, but also in formation of imides which is unacceptable. Transesterification with acetoxybenzenesulfonic acid or its salt avoids imide formation.

The overall processes herein comprising either Sequences 1–3, Sequences 1 and 4, or Sequences 1 and 5 have several advantages, including one or more of: low cost starting materials; minimum number of reaction steps; good yields for each step; reasonable reaction times; no waste byproducts; ability to recycle starting materials; and no solids handling until the last step.

The following Examples further illustrate the invention but are not intended to be limiting thereof.

Analytical

GC Analysis Method. This method is applicable to the determination of the relative content of octanoic acid, decanoic acid, octanoic acid phenyl ester, octanoyl caprolactam, 2-pyrrolidinone, octanoyl diamido acid, phenylesters of $C_8$–$C_{10}$ amidocaproic acid, $C_8$ amidobutyric acid, caprolactam, 6-aminocaproic acid, $C_8$–$C_{10}$ amidocaproic acid, and phenol, in reaction samples.

The components listed above are separated, after silylation, by temperature programmed GC on a 15 m DB 1 column. A hot (300° C.) split injector is used and detection is by FID. GC area % is used to estimate content of components in a sample. The materials containing active hydrogens are derivatized with BSTFA containing 1% TMCS.

Chemicals:

Reagents

Pyridine

N,O-bis (trimethylsilyl)trifluoroacetamide with 1% trimethylchlorosilane

Equipment:

| Equipment Description | Source |
|---|---|
| Hewlett Packard 5890 GC | Hewlett Packard |
| HP7673 split injection | |
| flame ionization detector | |
| Column: 15 m, DB-1, 0.25 mm ID, .25u | J&W Scientific |

Procedure:

1. Standard Preparation: (See sample preparation below to make retention time standard solutions.)
2. Sample Preparation: Weigh 5–10 mg sample into a GC vial, add 1.0 mL derivatization grade pyridine and 0.6 mL BSTFA (w/1% TMCS), seal vial, and heat at 70° C. for 30 minutes.

| 3. Instrument Settings | | 4. Approximate Retention Times: | |
|---|---|---|---|
| a) Split injection | On | Phenol | 6.3 |
| | | 2-Pyrrolidinone | 7.6 |
| b) Split ratio | About 30:1 | Caprolactam | 10.0 (185)* |
| c) Column flow | 1 mL/min. | Octanoic acid | 10.3 |

| 3. Instrument Settings | | 4. Approximate Retention Times: | |
|---|---|---|---|
| d) Purge flow | 0.5 mL/min. | Decanoic acid | 13.6 |
| e) Injection volume | 1 uL | 6-aminocaproic acid | 14.3, 17.9 (347)* |
| f) Injector temperature | 300° C. | Octanoic acid phenyl ester | 16.4 |
| | | Octanoyl amidobutyric acid | 17.3 |
| g) Inlet oven tracking | Off | Octanoyl caprolactam | 19.5 (239)* |
| h) FID detector temperature | 330° C. | Octanoyl amido caproic acid | 23.2, 24.0 (329)* |
| i) Oven initial temperature | 50° C. | Decanoyl amido caproic acid | 25.3, 26.2 |
| j) Oven ramp rate | 8.0° C./min. | Hexanoyl amido acid phenyl ester | 25.7 |
| k) Oven final temperature | 325° C. | Octanoyl amido acid phenyl ester | 27.6 (333)* |
| l) Oven final hold time | 4.63 min. | Decanoyl amino acid phenyl ester | 29.6, 30.5 |
| | | Octanoyl diamido acid | 31.4, 32.4 (442)* |

*Molecular weight of GC component.

4. Calculation of Mole % Conversion: The GC relative area % for each component derived from caprolactam is divided by its molecular weight or the molecular weight of its trimethylsilyl derivative to give a relative mol %. The relative mol % for all components derived from caprolactam are summed to give a total relative mol %. Finally, each relative mol % is divided by the total relative mol % to give mol % conversion. An analogous procedure is used to calculate mol % conversion of amido acid to amido acid phenyl ester.

AMIDATION EXAMPLES I–XV

Synthesis of C8-Amidocaproic Acid—A 100 mL, 3-neck, round bottom flask is fitted with thermometer, condenser, magnetic stir bar, and a purge tube through which nitrogen is passed through the reaction mixture. The reaction vessel is charged with caprolactam (4.00 g, 0.036 mol, 1 mol equivalent), octanoic acid, the indicated strong acid catalyst (TSA, MSA, PSA, PPA, SA, as described in the tables), and optionally boric acid. The reaction is kept at the designated temperature for 4 hours using a high temperature oil bath, continuously purging with nitrogen. After 4 hour reaction time, the reaction mixture is analyzed by GC (see GC Analysis Method) to determine % conversion of caprolactam to amido acid (see Table 1). Reaction mixture color after 4 hours is also noted.

TABLE 1

Amidation Results

| Example # | I | II | III | IV | V |
|---|---|---|---|---|---|
| Octanoid-acid (mol equivalent) | 4 | 4 | 4 | 4 | 2 |
| Strong acid catalyst* (mol equivalent) | 0.1 TSA | 0.05 TSA | 0.1 TSA | 0.05 TSA | 0.1 TSA |
| Boric acid (mol equivalent) | — | 0.05 | — | — | — |
| Water (mol equivalent) | — | — | — | 0.2 | — |
| Temperature (°C.) | 200 | 200 | 175 | 220 | 200 |
| Reaction color after 4 hr | brown | brown | yellow | brown | brown |
| GC Relative Area % for Components | | | | | |
| Caprolactam | 3.59 | 3.82 | 10.33 | 3.56 | 9.09 |
| Octanoic acid | 74.97 | 73.23 | 79.21 | 74.79 | 62.96 |
| 6-aminocaproic acid | 0.12 | 0 | 1.12 | 0.26 | 0 |
| Octanoylcaprolactam | 2.37 | 3.02 | 0.94 | 3.67 | 1.48 |
| Octanoyl amido acid | 15.95 | 17.24 | 6.49 | 15.6 | 19.1 |
| Octanoyl diamido acid | 1.63 | 1.21 | 0.62 | 0.89 | 5.07 |
| Mole % Conversion of Caprolactam to Components | | | | | |
| Caprolactam | 23.7 | 23.3 | 66.4 | 22.9 | 39.3 |
| 6-aminocaproic acid | 0.4 | 0 | 3.9 | 0 | 0 |
| Octanoylcaprolactam | 12.1 | 14.3 | 4.7 | 18.3 | 5.0 |
| Octanoyl amido acid | 59.2 | 59.3 | 23.4 | 56.4 | 46.5 |
| Octanoyl diamido acid | 4.5 | 3.1 | 1.7 | 2.4 | 9.2 |

TABLE 1-continued

Amidation Results

| Example # | VI | VII | VIII | IX | X |
|---|---|---|---|---|---|
| Octanoic acid (mol equivalent) | 4 | 4 | 4 | 4 | 4 |
| Strong acid catalyst* (mol equivalent) | 0.05 MSA | 0.05 MSA | 0.05 MSA | 0.05 PSA | 0.05 PPA |
| Boric acid (mol equivalent) | — | — | 0.05 | 0.05 | — |
| Water (mol equivalent) | — | 0.2 | — | — | — |
| Temperature (°C.) | 200 | 200 | 200 | 200 | 200 |
| Reaction color after 4 hr | brown | brown | yellow | black | yellow |
| GC Relative Area % for Components | | | | | |
| Caprolactam | 5.08 | 3.86 | 3.68 | 8.99 | 6.64 |
| Octanoic acid | 73.5 | 74.06 | 72.36 | 78.29 | 71.82 |
| 6-aminocaproic acid | 0 | 0 | 0 | 0.60 | 0 |
| Octanoylcaprolactam | 3.41 | 2.40 | 3.08 | 1.26 | 4.02 |
| Octanoyl amido acid | 15.75 | 17.07 | 17.35 | 8.91 | 15.03 |
| Octanoyl diamido acid | 0.90 | 1.23 | 2.02 | 0.62 | 0.98 |
| Mole % Conversion of Caprolactam to Components | | | | | |
| Caprolactam | 30.0 | 24.4 | 22.1 | 57.8 | 35.7 |
| 6-aminocaproic acid | 0 | 0 | 0 | 2.1 | 0 |
| Octanoylcaprolactam | 15.6 | 11.7 | 14.3 | 6.3 | 16.7 |
| Octanoyl amido acid | 52.2 | 60.6 | 58.5 | 32.2 | 45.4 |
| Octanoyl diamido acid | 2.2 | 3.3 | 5.1 | 1.7 | 2.2 |

| Example # | XI | XII | XIII | XIV | XV |
|---|---|---|---|---|---|
| Octanoic acid (mol equivalent) | 4 | 4 | 4 | 4 | 1 |
| Strong acid catalyst* (mol equivalent) | 0.01 SA | 0.05 SA | 0.05 SA | 0.24 SA | 0.01 SA |
| Boric acid (mol | 0.05 | 0.05 | 0.05 | 0.05 | 0.05 |

TABLE 1-continued

Amidation Results

| equivalent) | | | | | |
|---|---|---|---|---|---|
| Water (mol equivalent) | — | 1 | 0.2 | 0.4 | — |
| Temperature (°C.) | 210 | 200 | 200 | 200 | 200 |
| Reaction color after 4 hr | black | yellow | black | black | black |
| GC Relative Area % for Components | | | | | |
| Caprolactam | 3.22 | 7.54 | 3.88 | 2.6 | 21.16 |
| Octanoic acid | 72.41 | 78.54 | 73.68 | 78.24 | 40.65 |
| 6-aminocaproic acid | 0.14 | 1.47 | 0.44 | 2.41 | 0.22 |
| Octanoylcaprolactam | 2.33 | 0.17 | 0.51 | 0.33 | 0.46 |
| Octanoyl amido acid | 17.46 | 9.53 | 18.21 | 13.58 | 23.34 |
| Octanoyl diamido acid | 2.61 | 1.28 | 2.46 | 1.38 | 9.85 |
| Mole % Conversion of Caprolactam To Components | | | | | |
| Caprolactam | 20.2 | 52.6 | 24.6 | 21.0 | 53.5 |
| 6-aminocaproic acid | 0 | 5.5 | 1.5 | 10.4 | 0.3 |
| Octanoylcaprolactam | 11.3 | 0.9 | 2.5 | 2.0 | 0.9 |
| Octanoyl amido acid | 61.6 | 37.4 | 64.9 | 61.8 | 33.2 |
| Octanoyl diamido acid | 6.9 | 3.7 | 6.5 | 4.7 | 10.4 |

*Key to abbreviations: TSA (toluenesulfonic acid monohydrate 99%), MSA (methanesulfonic acid 99%), SA (sulfuric acid 98%), PSA (phenolsulfonic acid 65%), PA (polyphosphoric acid)

EXAMPLES XVI–XVIII

Synthesis of C8-Amidocaproic Acid—A 100 ml, 3-neck round bottom flask is fitted with thermometer, condenser, magnetic stir bar, and a sparge tube through which nitrogen is passed through the reaction mixture. The reaction vessel is charged with caprolactam (4.00 g, 0.036 mol, 1 mol equivalent), octanoic acid, boric acid, and water. The reaction is kept at the designated temperature for 3.5 hr using a high temperature oil bath, continuously sparging with nitrogen. After 3.5 hr reaction time, the reaction mixture is analyzed by GC (see GC Analysis Method) to determine % conversion of the caprolactam to amido acid (see Table 2). Other products formed are 6-aminocaproic acid, octanoyl caprolactam, and octanoyl diamido acid. Reaction mixture color after 3.5 hr is also noted:

TABLE 2

Amidation Results

| Example # | XVI | XVII | XVIII |
|---|---|---|---|
| Octanoic acid (mol equivalent) | 4 | 8 | 2 |
| boric acid (mol equivalent) | 0.025 | 0.05 | 0.025 |
| water (mol equivalent) | 0.1 | 0.1 | 0.1 |
| temperature (°C.) | 235 | 220 | 235 |
| reaction color after 4 hours | yellow | yellow | orange |
| GC Relative Area % for Components | | | |
| caprolactam | 3.46 | 1.39 | 6.42 |
| octanoic acid | 71.57 | 85.06 | 55.01 |
| 6-aminocaproic acid | 0 | 0 | 0 |
| octanoylcaprolactam | 4.71 | 1.18 | 3.49 |
| octanoyl amido acid | 15.44 | 10.33 | 26.09 |
| octanoyl diamido acid | 1.74 | 0.39 | 5.37 |
| Mole % Conversion of Caprolactam to Components | | | |
| caprolactam | 20.9 | 16.8 | 24.7 |
| 6-aminocaproic acid | 0 | 0 | 0 |
| octanoylcaprolactam | 22.1 | 11.1 | 10.4 |
| octanoyl amido acid | 52.6 | 70.2 | 56.3 |
| octanoyl diamido acid | 4.4 | 2.0 | 8.6 |

EXAMPLES XIX–XX

Synthesis of C8-Amidocaproic Acid—A 100 ml, 3-neck round bottom flask is fitted with thermometer, condenser, magnetic stir bar, and a sparge tube through which nitrogen is passed through the reaction mixture. The reaction vessel is charged with caprolactam (4.00 g, 0.036 mol, 1 mol equivalent), octanoic acid, methanesulfonic acid, and boric acid. The reaction is kept at the designated temperature for 6.5 hr using a high temperature oil bath, continuously sparging with nitrogen. The reaction is then allowed to cool to room temperature and water is added. The reaction is allowed to stir at room temperature for 18 hr. Before water addition (Example XIX) and 18 hr after water addition (Example XX), the reaction mixture is analyzed by GC (see GC Analysis Method) to determine % conversion of caprolactam to amido acid (see Table 3). Other products formed are 6-aminocaproic acid, octanoyl caprolactam, and octanoyl diamido acid. Reaction mixture color is also noted.

TABLE 3

Amidation Results

| Example # | XIX | XX |
|---|---|---|
| Octanoic acid (mol equivalent) | 9.28 | 9.28 |
| boric acid (mol equivalent) | 0.05 | 0.05 |
| water (mol equivalent) | — | 0.1 |
| methanesulfonic acid (mol equivalent) | 0.1 | 0.01 |
| temperature (°C.) | 235 | 250 |
| reaction color | orange | orange |
| GC Relative Area % for Components | | |
| caprolactam | 0.60 | 1.39 |
| octanoic acid | 84.89 | 85.06 |
| 6-aminocaproic acid | 0 | 0 |
| octanoylcaprolactam | 2.75 | 1.18 |
| octanoyl amido acid | 6.36 | 10.33 |
| octanoyl diamido acid | 0 | 0.39 |
| Mole % Conversion of Caprolactam to Components | | |
| caprolactam | 9.5 | 16.8 |
| 6-aminocaproic acid | 0 | 0 |
| octanoylcaprolactam | 33.8 | 11.1 |
| octanoyl amido acid | 56.8 | 70.2 |
| octanoyl diamido acid | 0 | 2.0 |

EXAMPLE XXI

Synthesis of C8 Amidobutyric Acid—A 100 mL, 3-neck, round bottom flask is fitted with thermometer, condenser, magnetic stir bar, and a purge tube through which nitrogen is passed through the reaction mixture. The reaction vessel is charged with 2-pyrrolidinone (2.00 g, 0.024 mol), octanoic acid (13.56 g, 0.094 mol), and sulfuric acid 98% (0.12 g, 0.0012 mol). The reaction is kept at 200° C. for 4 hours using a high temperature oil bath, continuously purging with nitrogen. After 4 hour reaction time, the reaction mixture is analyzed by GC (see Table 2). A 31% conversion of pyrrolidinone to amido acid is obtained. The reaction mixture is brown after 4 hours.

TABLE 4

Amidation Results with 2-Pyrrolidinone

| GC Relative Area % for Components | |
|---|---|
| 2-pyrrolidinone | 8.63 |
| Octanoic acid | 82.39 |
| Octanoyl amido acid | 7.54 |
| Mole % Conversion of 2-Pyrrolidinone to Components | |
| 2-pyrrolidinone | 68.8 |
| Octanoyl amido acid | 31.2 |

EXAMPLE XXII

Scale-up Synthesis of $C_8$ Amidocaproic Acid—A 250 mL, 3-neck, round bottom flask is fitted with thermometer, condenser, magnetic stir bar, and a purge tube through which nitrogen is passed through the reaction mixture. The reaction vessel is charged with caprolactam (15.00 g, 0.131 mol), octanoic acid (76.10 g, 0.525 mol), and p-toluenesulfonic acid (1.26 g, 0.0065 mol). The reaction is kept at 200° C. for 4 hours using a high temperature oil bath, continuously purging with nitrogen. After 4 hours reaction time, the reaction mixture is analyzed by GC to determine % conversion of caprolactam to amido acid (see Table 5). Reaction mixture is brown after 4 hours. Caprolactam and octanoic acid are removed by vacuum distillation (90°–100° C., 4.3 mm) to give the desired C8 amido acid as a brown solution (20.8 g) with the analysis as shown in Table 5.

TABLE 5

Amidation Results of Scale-up Reaction

| GC Relative Area % for Components | Reaction Mixture | Product (after distillation) |
|---|---|---|
| Caprolactam | 6.36 | 3.61 |
| Octanoic acid | 76.18 | 1.22 |
| 6-aminocaproic acid | 0.28 | 0.56 |
| Octanoylcaprolactam | 1.12 | 1.26 |
| Octanoyl amido acid | 14.43 | 76.04 |
| Octanoyl diamido acid | — | 12.62 |

| Mole % Conversion of Caprolactam to Components (before distillation) | |
|---|---|
| Caprolactam | 41.1 |
| 6-aminocaproic acid | 1.0 |
| Octanoylcaprolactam | 5.6 |
| Octanoyl amido acid | 52.4 |

In addition to the above, the amidation reaction can be conducted using benzoic acid and caprolactam with methanesulfonic acid plus boric acid to provide benzoyl-amide caproic acid

ESTERIFICATION EXAMPLES XXIII–XXVI

Synthesis of C8 Amidocaproic Acid Phenyl Ester—A 100 mL, 3-neck, round bottom flask is fitted with thermometer, Dean-Stark trap with condenser, magnetic stir bar, and a purge tube through which nitrogen is passed through the reaction mixture. The reaction vessel is charged with C8 amido acid—made from C8 acid chloride and aminocaproic acid—(10 g, 0.037 mol, 1 mol equivalent), phenol, sulfuric acid 98%, and boric acid. The reaction is kept at 180°–195° C. for 4 hours using a high temperature oil bath held at 205°–210° C., continuously sparging with nitrogen. Some of the phenol is optionally removed with a Dean-Stark trap. After 4 hours reaction time, the reaction mixture is analyzed by GC (see GC Analysis Method) to determine % conversion of C8 amidocaproic acid to C8 amidocaproic acid phenyl ester (see Table 6). Other products formed are caprolactam, octanoic acid, octanoic acid phenyl ester, 6-aminocaproic acid. Reaction mixture color after 4 hours is noted.

TABLE 6

Esterification Results with C8 Amidocaproic Acid

| Example # | XXIII | XXIV | XXV |
|---|---|---|---|
| Phenol (mol equivalent) | 20 | 5.7 | 15 |
| Sulfuric acid (mol equivalent) | 0.25 | 0.25 | 0.05 |
| Boric acid (mol equivalent) | 0.07 | 0.07 | 0.05 |
| % phenol removed | 50% removed during first 40 min | 50% removed during first 30 min | no phenol removed |
| Reaction color after 4 hr | orange | orange | yellow |
| GC Relative Area % for Components | | | |
| Caprolactam | 1.28 | 10.16 | 7.41 |
| Octanoic acid | 0.12 | 4.22 | 1.87 |
| 6-aminocaproic acid | 0.1 | 0.39 | 1.61 |
| Octanoic acid phenyl ester | 4.71 | 28.89 | 16.33 |
| Octanoylcaprolactam | 0.91 | 1.18 | 2.62 |
| Octanoyl amido acid | 0.58 | 8.9 | 46.39 |
| Octanoyl amido acid phenyl ester | 82.04 | 37.07 | 23.76 |
| Octanoyl diamido acid | 3.95 | 0 | 0 |
| Octanoyl diamido acid phenyl ester | 0 | 2.71 | 0 |
| Mole % Conversion of Amido Acid to Components | | | |
| Caprolactam | 3.7 | 15.4 | 11.4 |
| 6-aminocaproic acid | 0.3 | 0.3 | 1.3 |
| Octanoic acid phenyl ester | 13.2 | 36.8 | 21.2 |
| Octanoylcaprolactam | 1.1 | 1.4 | 3.1 |
| Octanoyl amido acid | 1.2 | 7.6 | 40.2 |
| Octanoyl amido acid phenyl ester | 76.2 | 31.3 | 20.3 |
| Octanoyl diamido acid | 3.8 | 0 | 0 |
| Octanoic acid | 0.4 | 5.5 | 2.5 |
| Octanoyl diamido acid phenyl ester | 0 | 1.7 | 0 |

| Example # | XXVI |
|---|---|
| Phenol (mol equivalent) | 20 |
| Sulfuric acid (mol equivalent) | 0.25 |
| Boric acid (mol equivalent) | 0.07 |
| % phenol removed | 50% removed during first 40 min |
| Reaction color after 4 hr | yellow |
| GC Relative Area % for Components | |
| Caprolactam | 3.60 |
| Octanoic acid | 0.37 |
| 6-aminocaproic acid | 0 |
| Octanoic acid phenyl ester | 12.54 |
| Octanoylcaprolactam | 1.36 |
| Octanoyl amido acid | 5.95 |
| Octanoyl amido acid phenyl ester | 67.46 |
| Octanoyl diamido acid | 2.14 |
| Mole % Conversion of Octanoyl Amido Acid to Components | |

TABLE 6-continued

Esterification Results with C8 Amidocaproic Acid

| | |
|---|---|
| Caprolactam | 6.3 |
| 6-aminocaproic acid | 0 |
| Octanoic acid phenyl ester | 18.4 |
| Octanoylcaprolactam | 1.8 |
| Octanoyl amido acid | 5.8 |
| Octanoyl amido acid phenyl ester | 65.5 |
| Octanoyl diamido acid | 1.6 |
| Octanoic acid | 0.6 |

EXAMPLE XXVII

Scale-up Synthesis of C8 Amidocaproic Acid Phenyl Ester—A 250 mL, 3-neck, round bottom flask is fitted with thermometer, condenser, magnetic stir bar, and a sparge tube through which nitrogen is passed through the reaction mixture. The reaction vessel is charged with C8 amidocaproic acid—product of Example 17—(20.8 g, 0.081 mol), phenol (152.3 g, 1.62 mol), sulfuric acid 98% (2.03 g, 0.02 mol), and boric acid (0.35 g, 0.0057 mol). The reaction is kept at 200° C. for 4 hours using a high temperature oil bath, continuously purging with nitrogen. During the first hour. of reaction time, 50 mL of phenol is removed via the Dean-Stark trap. After 4 hours reaction time, the reaction mixture is analyzed by GC to determine % conversion of C8 amidocaproic acid to C8 amidocaproic acid phenyl ester (see Table 5). Reaction mixture is brown after 4 hours. Phenol is removed by vacuum distillation (90°–100° C., 4.3 mm) to give the desired C8 amido acid phenyl ester as a brown solution (31.6 g) with the analysis shown in Table 7.

TABLE 7

Esterification Results of Scale-up Reaction

| | Reaction Mixture | Product (after distillation) |
|---|---|---|
| GC Relative Area % for Components | | |
| Caprolactam | 3.47 | 3.97 |
| Octanoic acid | 0 | 0 |
| 6-aminocaproic acid | 0 | 0.29 |
| Octanoic acid phenyl ester | 8.33 | 5.29 |
| Octanoylcaprolactam | 1.17 | 0 |
| Octanoyl amido acid | 3.68 | 0 |
| Octanoyl amido acid phenyl ester | 48.77 | 63.07 |
| Octanoyl diamido acid | 10.08 | 11.10 |
| Octanoyl diamido acid phenyl ester | 2.07 | 8.22 |
| Mole % Conversion of Caprolactam to Components | | |
| Caprolactam | 7.5 | 7.7 |
| 6-aminocaproic acid | 0 | 0 |
| Octanoic acid phenyl ester | 15.1 | 8.6 |
| Octanoylcaprolactam | 2.0 | 0 |
| Octanoyl amido acid | 4.5 | 0 |
| Octanoyl amido acid phenyl ester | 60.1 | 67.8 |
| Octanoyl diamido acid | 9.1 | 9.0 |
| Octanoyl diamido acid phenyl ester | 1.8 | 6.6 |

SULFONATION EXAMPLE XXVIII

Synthesis of C8 Amidocaproic Acid Phenyl Ester Sulfonate—C8 Amidocaproic acid phenyl ester (22.00 g, 0.0634 mol) is placed in 100 mL 2-neck round-bottom fitted with a glass tube reaching the bottom of the flask and a condenser connected to a bubbler. The flask is heated to 50° C. in an oil bath to melt the phenyl ester. Sulfur trioxide (5.0 g, 2.6 mL, 0.0634 mol) vapor diluted with nitrogen is added to the reaction over 1 hour through the glass tube. [The glass tube is connected via Teflon tubing to another flask heated at 65° C. in which liquid sulfur trioxide is placed. Nitrogen is bubbled through the liquid sulfur trioxide to obtain the gas mixture.] The reaction is then heated at 50° C. for an additional 30 minutes after the sulfur trioxide addition. The reaction is allowed to cool to room temperature and then poured into saturated aqueous sodium bicarbonate. The product precipitates as a white solid and is collected by vacuum filtration. After drying, the product (17.7 g) is obtained in 65% yield.

TRANSESTERIFICATION EXAMPLE XXIX

Synthesis of C10 Amidocaproic Acid Phenyl Ester—Amido acid (1.00 g, 0.0039 mol), phenyl acetate (1.59 g, 0.012 mol), and sodium acetate (0.032 g, 0.00039 mol) are placed in a 100 mL round-bottom flask fitted with condenser. The solution is heated at 210 C for 0.5 hr under nitrogen. Then acetic acid and excess phenyl acetate are removed by vacuum distillation with a Kugelrohr apparatus. The product (1.10 g) is obtained as a white solid which contains unreacted amido acid and excess phenyl acetate. HNMR of crude reaction mixture indicates ~75% yield (by integration ratio of the 2.58 ppm resonance—$CH_2C(=O)OPh$—to the 3.16 resonance—$C(=O)NHCH_2$).

TRANSESTERIFICATION EXAMPLE XXX

Synthesis of C10 Amidocaproic Acid Phenyl Ester Sulfonate—Into a 100 mL, 3 neck round bottom flask fitted with a nitrogen sparge tube, magnetic stirrer, Dean-Stark trap with condenser, and thermometer, is added C10 amido acid (48.5 g, 0.17 mol), sodium acetoxybenzenesulfonate (15 g, 0.057 mol), and sodium acetate (0.94 g, 0.114 mol). The reaction is kept at 200° C. for 3 hr using a high temperature oil bath held at 205°–210° C., continuously sparging with nitrogen. Distillate (7 mL) is collected in the Dean-Stark trap. The reaction is poured hot into a mortar and after cooling is ground into a powder. HNMR of crude reaction mixture indicates ~90% yield (by integration ratio of the 2.58 ppm resonance—$CH_2C(=O)OPhSO_3Na$—to the 3.16 resonance—$C(=O)NHCH_2$). The reaction mixture is recrystallized from methanol (370 mL) to obtain a first crop (15.1 g) and a second crop (4.7 g) of desired product (75% recrystallized yield based on sodium acetoxybenzenesulfonate).

ESTERIFICATION EXAMPLE XXXI

Synthesis of C10 Amidocaproic Acid Phenyl Ester Sulfonate—Into a 100 mL, 3 neck round bottom flask fitted with a nitrogen sparge tube, magnetic stirrer, Dean-Stark trap with condenser, and thermometer, is added C10 amido acid (3.5 g, 0.0123 mol), acetic anhydride (0.46 g, 0.0045 mol), and methanesulfonic acid (0.002 g, 0.00002 mol). The reaction mixture is heated at 100° C. for 2 hr. to form the amido acid anhydride. Then anhydrous sodium phenolsulfonate (0.80 g, 0.0041 mol) and sodium acetate (0.017 g, 0.0002 mol) is added and the reaction heated at 180° C. for 1.5 hr. At the beginning the reaction is fluid, but at the end it is a thick paste. HNMR of crude reaction mixture indicates ~70% yield (by integration ratio of the 2.58 ppm resonance—$CH_2C(=O)OPh$—to the 3.16 resonance—$C(=O)NHCH_2$).

ESTERIFICATION EXAMPLE XXXII

Synthesis of C8 Amidocaproic Acid Phenyl Ester Sulfonate—Into a 250 mL, 3 neck round bottom flask fitted with a nitrogen sparge tube, magnetic stirrer, Dean-Stark trap with condenser, and thermometer, is added C8 amidocaproic acid (10.0 g, 0.039 mol), acetic anhydride (17.9 g, 0.175 mol), sodium acetate (0.16 g, 0.002 mol), and imidazole (0.13 g, 0.002 mol). The reaction mixture is heated at 110° C. for 3 hr with a nitrogen sparge; 10 mL of distillate is collected in the Dean-Stark trap. Then acetic acid and excess acetic anhydride is removed by vacuum distillation to obtain amido acid anhydride. The crude amido acid anhydride is dispersed in ether (60 mL), filtered, and dried to obtain nearly pure amido acid anhydride (indicated by HNMR) as a white solid (8.6 g).

Into a 100 mL, 3 neck round bottom flask fitted with a nitrogen sparge tube, magnetic stirrer, condenser, and thermometer, is added a portion of the pure amido acid anhydride (3.5 g, 0.0071 mol), anhydrous sodium phenolsulfonate (1.11 g, 0.0056 mol), sodium acetate (0.029 g, 0.0004 mol), and toluene (12 mL). The reaction is refluxed 3 hr 180° C. A small, homogeneous aliquot of the reaction mixture is taken and evaporated for HNMR analysis. HNMR indicates 75% yield based on sodium phenolsulfonate (by integration ratio of the 2.58 ppm resonance—$CH_2C(=O)OPh$—to the 3.16 resonance—$C(=O)NHCH_2$). Then additional toluene (50 mL) is added, the reaction mixture filtered hot, and the precipitate dried to obtain the desired product as a white solid (2.6 g) which is 54% pure by HNMR (by integration ratio of the 2.58 ppm resonance—$CH_2C(=O)OPh$—to the 3.16 resonance—$C(=O)NHCH_2$). The remainder of the material is amido acid, sodium phenol sulfonate, and acetoxybenzenesulfonate.

The following illustrates the use of the amido acids and bleach activators of this invention in otherwise conventional consumer goods, but is not intended to be limiting thereof.

EXAMPLE XXXIII

A mild lubricious soap bar composition is prepared in conventional extrusion apparatus, as follows. The bar resists dry cracking and wet smear.

| Ingredient | Percent (wt.) |
|---|---|
| $C_{16-18}$ fatty acid soap* | 78.0 |
| Amido acid** | 6.0 |
| NaCl/KCl (1:1 wt.) | 0.5 |
| $C_{12}H_{33}C(O)N$-methylglucamide | 8.0 |
| Water and minors | Balance |

*1:1 (wt.) mixture of Na and K soaps
**Per Example I, above.

EXAMPLE XXXIII

A laundry bleaching system suitable for use alone or in admixture with a conventional granular laundry detergent is as follows.

| Ingredient | Percent (wt.) |
|---|---|
| Sodium percarbonate | 90.0 |
| Bleach activator* | 10.0 |

*Per Example XXVIII, above.

The foregoing composition can be added to water at levels of 100 ppm, and above, to provide a fabric bleaching action.

What is claimed is:

1. A method for preparing bleach activators which are amido acid phenyl ester sulfonates, or mixtures thereof, of the formulas:

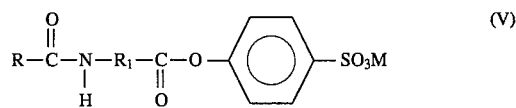

and

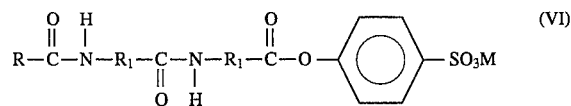

wherein R is a $C_1$–$C_{21}$ hydrocarbyl substituent and $R^1$ is a $C_2$–$C_{10}$ hydrocarbylene substituent, the sulfonate group is ortho or para substituted, and M is a cation moiety, said method comprising sulfonating and neutralizing an amido acid phenyl ester selected from the formulas:

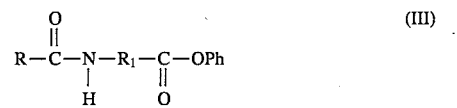

and

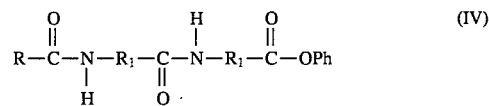

prepared by a method comprising:

(a) preparing an amido acid, or mixture thereof, of the formulas

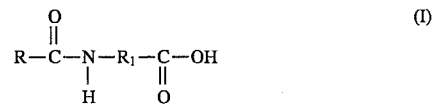

and

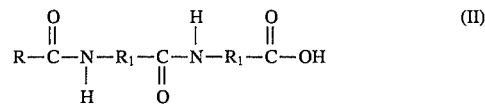

by reacting in the presence of an acid catalyst a carboxylic acid of the formula

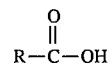

with a lactam of the structure

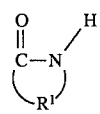

wherein R and $R^1$ are as described before; and (b) reacting the amido acid, or mixture thereof, of step (a) with phenol in the presence of a strong acid catalyst and boric acid.

2. A method according to claim 1 wherein R is $C_6$–$C_{17}$ and $R^1$ is $(CH_2)_x$ wherein x is from 2 to 5.

3. A method for preparing bleach activators which are amido acid phenyl ester sulfonates, or mixtures thereof, of the formulas:

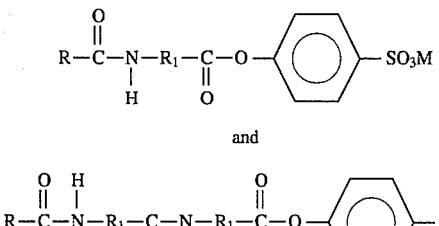

wherein R is a $C_1$–$C_{21}$ hydrocarbyl substituent and $R^1$ is a $C_2$–$C_{10}$ hydrocarbylene substituent, the sulfonate group is ortho or para substituted, and M is a cation moiety, said method comprising sulfonating and neutralizing an amido acid phenyl ester selected from the formulas:

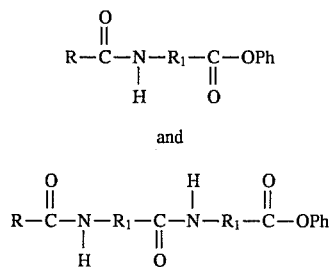

prepared by a method comprising:

(a) preparing an amido acid, or mixture thereof, of the formulas

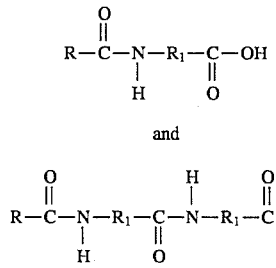

by reacting in the presence of an acid catalyst a carboxylic acid of the formula

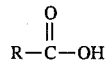

with a lactam of the structure

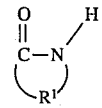

wherein R and $R^1$ are as described before; and (b) reacting the amido acid, or mixture thereof, of step (a) with a phenol ester of a lower molecular weight carboxylic acid moiety in the presence of a basic catalyst.

4. A method according to claim 3 wherein R is $C_6$–$C_{17}$ and $R^1$ is $(CH_2)_x$ wherein x is from 2 to 5.

5. A method for preparing bleach activators which are amido acid phenyl ester sulfonates, or mixtures thereof, of the formulas:

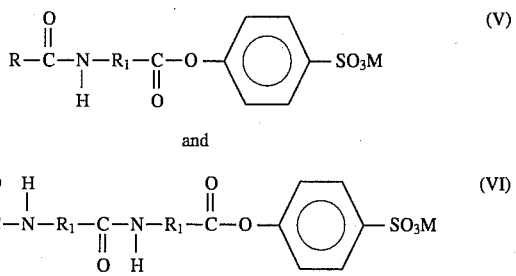

said method comprising (a) preparing an amido acid, or mixtures thereof, of the formulas:

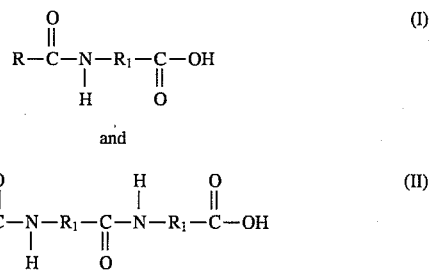

by reacting in the presence of an acid catalyst a carboxylic acid of the formula:

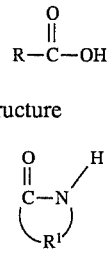

with a lactam of the structure and (b) reacting the amido acid, or mixtures thereof, of step (a) with an ester derivative of phenol sulfonic acid or salt of the formula:

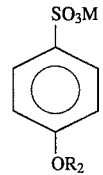

wherein in each of the above formulas R is a $C_1$–$C_{21}$ hydrocarbyl substituent, $R^1$ is a $C_2$–$C_{10}$ hydrocarbylene substituent, $R^2$ is an acid moiety, and M is a cationic moiety.

6. A method according to claim 5 wherein M is hydrogen and $R^2$ is a lower molecular weight carboxylic acid moiety.

7. A method according to claim 6 wherein R is $C_6$–$C_{17}$ and $R^1$ is $(CH_2)_x$ wherein x is from 2 to 5.

8. A method according to claim 5 wherein M is a member selected from monovalent metal salts and divalent metal salts, and $R^2$ is a lower molecular weight carboxylic acid moiety.

9. A method according to claim 8 wherein R is $C_6$–$C_{17}$ and $R^1$ is $(CH_2)x$ wherein x is from 2 to 5.

10. A method for preparing bleach activators which are amido acid phenyl ester sulfonates, or mixtures thereof, of the formulas:

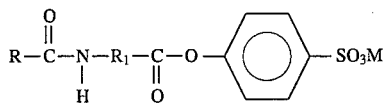
(V)

and

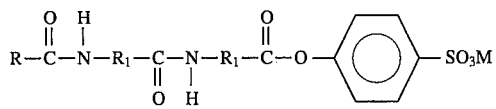
(VI)

said method comprising reacting an amido acid, or mixtures thereof, of the formulas:

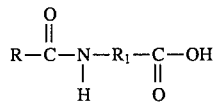
(I)

and

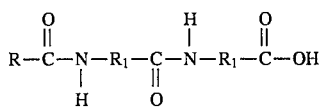
(II)

with an ester derivative of phenol sulfonic acid or salt of the formula:

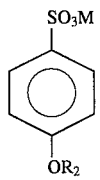

wherein in each of the above formulas R is a $C_1$ or higher hydrocarbyl substituent, $R^1$ is a $C_2$–$C_{10}$ hydrocarbylene substituent, $R^2$ is an acid moiety, and M is a cationic moiety.

11. A method for preparing bleach activators which are amido acid phenyl ester sulfonates, or mixtures thereof, of the formulas:

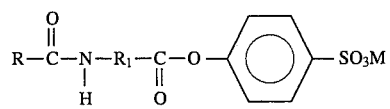
(V)

and

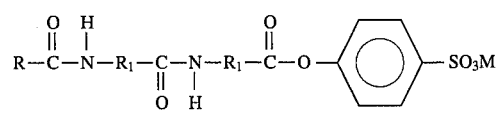
(VI)

said method comprising the steps of (a) preparing an amido acid, or mixture thereof, having the formulas:

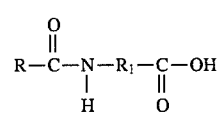
(I)

and

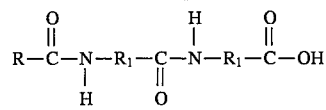
(II)

by reacting in the presence of an acid catalyst a carboxylic acid of the formula:

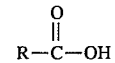

with a lactam of the structure

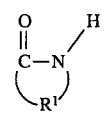

and (b) reacting the amido acid, or mixtures thereof, of step (a) with a lower molecular weight carboxylic acid anhydride to form the amido acid anhydride; and (c) reacting the amido acid anhydride, or mixture thereof, of step (b) with phenolsulfonate salt to form the amido acid phenyl ester sulfonate, wherein in each of the above formulas R is a $C_1$–$C_{21}$ hydrocarbyl substituent, $R^1$ is a $C_2$–$C_{10}$ hydrocarbylene substituent, and M is a cationic moiety.

12. A method according to claim 11 wherein in step (a) the lower molecular weight carboxylic acid anhydride is selected from anhydrides having the formula $(R^3CO)_2O$, wherein each $R^3$ is the same or different $C_1$–$C_4$ hydrocarbyl substituents.

13. A method according to claim 12 wherein the lower molecular weight carboxylic acid anhydride is acetic anhydride.

14. A method according to claim 11 wherein the molar ratio of amido acid to carboxylic acid anhydride is in the range from about 1:3 to 5:1.

15. A method according to claim 11 wherein in step (b) the amido acid anhydride is reacted with sodium phenolsulfonate salt.

16. A method according to claim 11 wherein R is $C_6$–$C_{17}$ and $R^1$ is $(CH_2)_x$ wherein x is from 2 to 5.

17. A method for preparing bleach activators which are amido acid phenyl ester sulfonates, or mixtures thereof, of the formulas:

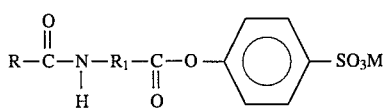
(V)

and

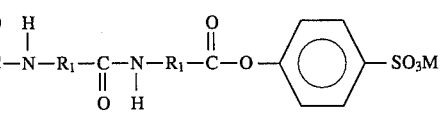
(VI)

said method comprising the steps of (a) reacting an amido acid, or mixture thereof, having the formulas:

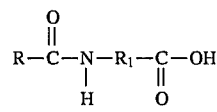 (I)

and

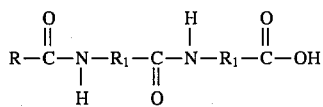 (II)

with a lower molecular weight carboxylic acid anhydride to form the amido acid anhydride; and (b) reacting the amido acid anhydride of step (a) with phenolsulfonate salt to form the amido acid phenyl ester sulfonate, wherein in each of the above formulas R is a $C_1$ or higher hydrocarbyl substituent, $R^1$ is a $C_2$–$C_{10}$ hydrocarbylene substituent, and M is a cationic moiety.

* * * * *

UNITED STATES PATENT AND TRADEMARK OFFICE
CERTIFICATE OF CORRECTION

PATENT NO. : 5,534,642
DATED : July 9, 1996
INVENTOR(S) : Stephen Wayne Heinzman et al.

It is certified that error appears in the above-indentified patent and that said Letters Patent is hereby corrected as shown below:

Column 24, in formulas V and VI extend the line connecting the $SO_3M$ moiety to the center of the phenyl ring Column 24, line 19, add "an" before --ortho-- and change "substituted" to --substituent--.

Column 25, in formulas V and VI extend the line connecting the $SO_3M$ moiety to the center of the phenyl ring Column 25, line 18, add "an" before --ortho-- and change "substituted" to --substituent--.

Signed and Sealed this

Seventh Day of January, 1997

Attest:

BRUCE LEHMAN

*Attesting Officer*  *Commissioner of Patents and Trademarks*